United States Patent [19]
Peredo

[11] Patent Number: 5,910,169
[45] Date of Patent: Jun. 8, 1999

[54] TOTAL MITRAL HETEROLOGOUS BIOPROSTHESIS TO BE USED IN MITRAL TRICUSPID HEART REPLACEMENT

[75] Inventor: Mario Osvaldo Vrandecic Peredo, Minas Gerais, Brazil

[73] Assignee: Newcor Industrial S.A., Brazil

[21] Appl. No.: 08/856,055

[22] Filed: May 14, 1997

Related U.S. Application Data

[63] Continuation of application No. 08/591,112, Jan. 25, 1996, abandoned, which is a continuation of application No. 08/313,406, Sep. 27, 1994, abandoned, which is a continuation of application No. 07/976,468, Nov. 16, 1992, abandoned.

[30] Foreign Application Priority Data

Jul. 28, 1992 [BR] Brazil .................. PI 9202905

[51] Int. Cl.[6] ...................................................... A61F 2/24
[52] U.S. Cl. .................................................................. 623/2
[58] Field of Search ........................................ 623/2, 900

[56] References Cited

U.S. PATENT DOCUMENTS

| | | | |
|---|---|---|---|
| 3,130,418 | 4/1964 | Head et al. | 623/2 |
| 4,035,849 | 7/1977 | Angell et al. | 623/2 |
| 4,261,342 | 4/1981 | Aranguren Duo | 623/2 |
| 4,769,032 | 9/1988 | Steinberg | 623/2 |
| 4,960,424 | 10/1990 | Grooters | 623/2 |
| 5,156,621 | 10/1992 | Navia et al. | 623/2 |
| 5,415,667 | 5/1995 | Frater | 623/2 |

*Primary Examiner*—Michael J. Milano
*Attorney, Agent, or Firm*—Hallie A. Finucane; Fish & Richardson P.C., P.A.

[57] ABSTRACT

The present invention relates to a heterologous total stentless mitral valve prosthesis for the use in mitral and tricuspid position which provides for better hemodynamic performance. This mitral valve prosthesis addresses the specific needs of flow and contractility, thereby prolonging durability. The heterologous total stentless mitral heart valve prosthesis of this present invention comprises one sewing ring, leaflets, and subvalvar apparatus having new chordal insertions which are fixed between two heterologous pericardial patches. This heart valve prosthesis is obtained from heterologous mammals, such as swine, ovine, bovine, and moreover, the pericardial patches used may also be of synthetic material. The heart valve prosthesis presents specific design benefits from its anatomical and functional characteristics permitting attachment of the chordae to the patient's papillary muscles and attachment of its sewing rim to the mitral annulus of the patient thereby providing for better hemodynamic performance and avoiding disfunction and dilatation.

6 Claims, 2 Drawing Sheets

TOTAL MITRAL HETEROLOGOUS BIOPROSTHESIS TO BE USED IN MITRAL TRICUSPID HEART REPLACEMENT

This is a continuation of application Ser. No. 08/591,112, filed Jan. 25, 1996, now abandoned, which is a continuation of application Ser. No. 08/313,406, filed Sep. 27, 1994, now abandoned, which is a continuation of application Ser. No. 07/976,468 filed Nov. 16, 1992 now abandoned.

FIELD OF THE INVENTION

The present invention relates to heart valve prostheses, and more specifically, to those used in the mitral and tricuspid positions, comprising a heterologous biological material total mitral valve device that may provide better durability and hemodynamic performance in the mitral or tricuspid position, according to the specific requirements of flow and contractility of the left ventricle.

BACKGROUND OF THE INVENTION

Rheumatic heart disease remains endemic in the developing countries and is responsible for diseases associated with heart valves, and typically the mitral valve, affecting in general the younger population.

The functional consequences of these lesions are valvar stenosis, insufficiency or mixed lesions, and exploratory surgical treatment. Further, because of the severity of the lesions to the valve components, reconstructive valvar surgery may not be possible. In this case, substitution or valve replacement surgery by a mechanical valve or a bioprosthesis (composite of prosthetic and biological materials) may be required.

Mechanical prosthesis, as shown in FIG. 1, have the advantage of better durability and the disadvantage of requiring life time anticoagulation and that in itself produces iatrogenic disease besides other complications such as hemorrhages, embolism and thromboembolism.

Bioprosthesis, as shown in FIG. 2, are made of a biological tissue mounted to a stent previously covered by a synthetic material in such a way as to provide a one way valve to reproduce to some extent the performance of a healthy human heart valve. Bioprosthesis have several advantages, such as, central flow, satisfactory hemodynamics, better quality of life, lower incidence of thromboembolism and bioprosthesis do not require the use of an anticoagulant.

The main drawback of the bioprosthesis is durability, especially in the younger population, due to the wear of the biological component, that is subject to high intraventricular pressures, and, in the case of the mitral valve; the current designs are not suitable to withstand high pressures and the specific flow pattern "VORTEX" of the left ventricle.

The natural mitral valve device includes a mitral annulus, mitral leaflets, subvalvar apparatus and the papillary muscles. The harmonic performance of this complex determines the adequacy of its intended function.

SUMMARY OF THE INVENTION

The current mitral heart valve prostheses are provided with a leaflet or disc fixed to a rigid stent or ring without the subvalvar and the papillary muscle components that are considered essential to the intended performance of the left ventricle as a unit.

The current mitral heart valve prostheses do perform well as a one way valve permitting adequate flow characteristics. However, the absence of the subvalvar apparatus and papillary muscles, which are fundamental elements to the preservation of the left ventricular function, contribute with time to sequelae, such as disfunctions and dilatation of the left ventricle.

It is the objective of the present invention to provide a more durable heterologous total stentless mitral valve prosthesis that will provide satisfactory hemodynamic performance in the mitral or tricuspid position. It is also an object of the present invention to provide a mitral valve prosthesis which complies with the left ventricular requirements of specific flow and contractility. This objective is accomplished by the heterologous total stentless mitral valve in the mitral and tricuspid positions of the present invention which has an anatomic and physiological design which provides the hemodynamic means for specific requirements of flow and contractility of the left ventricle in humans. Thus, the design avoids complications such as disfunction and dilatation of the left ventricle which thereby provides better quality of life for the recipient and durability in use.

BRIEF DESCRIPTION OF THE DRAWINGS

The invention is hereinafter described with reference to the accompanying drawings in which.

DETAILED DESCRIPTION OF THE INVENTION

Figure 1:
FIG. 1 illustrates a mechanical prosthesis of the prior art.
Figure 2:
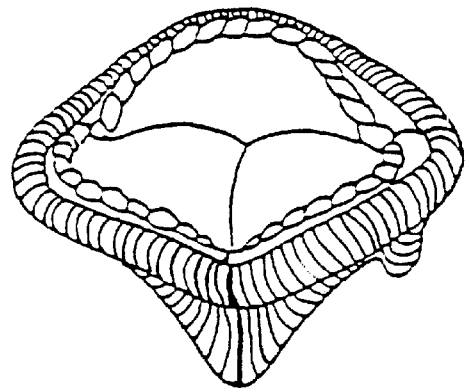
FIG. 2 shows a bioprosthesis also of the prior art.
Figure 3:
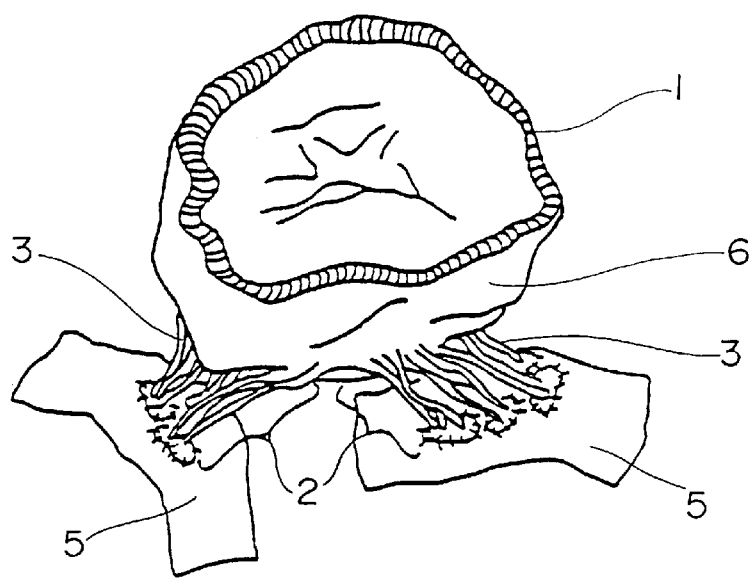
FIG. 3 illustrates a preferred embodiment of the heterologous total stentless mitral valve substitute of the present invention in the mitral and tricuspid position.
Figure 4:
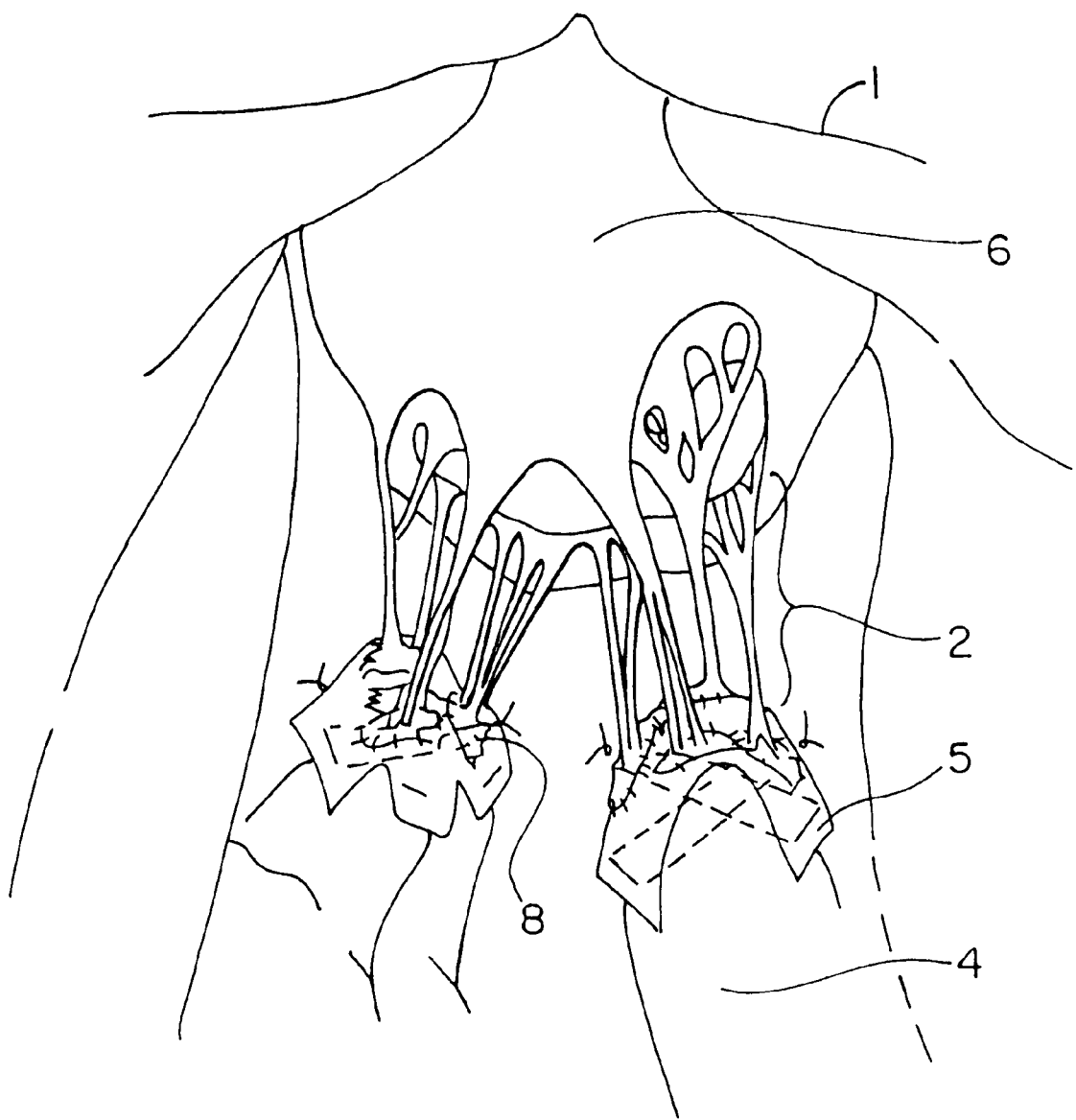
FIG. 4 illustrates the mitral valve prosthesis of FIG. 3 attached between the mitral annulus and papillary muscle of the patient.

As is shown in FIGS. 3 and 4, the heterologous total stentless mitral valve prosthesis to be used in mitral and tricuspid position of the present invention is illustrated. This mitral valve prosthesis is comprised of a mitral sewing rim (1), a complete subvalvar apparatus (2) with chordal attachments (3) which are naturally attached between mitral leaflets (6) and heterologous portion or slices (8) of the mammal's papillary muscle. The choral attachments (3) are fixed to a heterologous pericardial patch graft (5) or to a synthetic material, as described below, depending upon its geometry.

This heterologous device can be the native mitral valve obtained from any mammal of size, anatomy and similar function to the human heart, including, for example, swine, ovine, bovine and others.

This heterologous device is removed immediately after slaughtering of the animal by surgical technique. All of the mitral device is obtained and immersed into a balanced electrolyte, glutaraldehyde containing solution. Thereafter, the excess of muscle tissue is removed by a dissection procedure. Each procedure is performed so as to preserve the integrity of the mitral device. Continuing monitoring of the quality control of each element is done daily until the proper tanning and cross linking of the tissue is obtained by the balanced electrolyte glutaraldehyde containing solution.

In this device each individual chordae and chordal group (3) is preserved, naturally between mitral leaflets (6) and heterologous portions (8) of papillary muscle. These portions (8) of papillary muscle are affixed between two heterologous pericardial patches (5) or synthetic materials using mono or polyfilament sutures. This procedure properly anchors the chordal groups (3) between two pericardial patches (5), respecting the spatial geometry of the single or chordal group (3). As is shown in FIG. 4, the pericardial patches (5) are then sutured to the papillary muscle (4) of the patient.

This total biological device consists of a sewing rim (1), leaflets (6) and the subvalvar apparatus (2), having chordal attachments (3) which are affixed to the pericardium (5) or to synthetic material and used as a heart valve prosthesis for the mitral and tricuspid valve of humans.

This device presents a specific design that allows the anchoring of it to the papillary muscle (4) and to the patient's mitral annulus, providing for better hemodynamic performance and avoiding disfunction and dilatation of the left ventricle. As a result thereof, this device benefits the recipient's quality of life as well as the durability of the device during use.

This heterologous total stentless mitral heart valve prosthesis may provide better durability, since it has all the known elements necessary for the harmonic function of the mitral valve and left ventricle which are not present in previous heart valve prostheses.

While in the foregoing specification a detailed description of an embodiment of the invention has been described for the purpose of illustration, many variations in the details herein given may be made by those skilled in the art without departing from the spirit and scope of the invention.

What is claimed is:

1. A heterologous total biological stentless mitral valve prosthesis, said mitral valve prosthesis comprising:

a heterologous mitral sewing rim to be secured to the mitral annulus of a patient;

heterologous mitral leaflets extending from said heterologous mitral sewing rim;

a heterologous subvalvar apparatus comprising chordal attachments and heterologous portions of papillary muscle, with each chordal attachment being of a predetermined geometry equivalent to that of the patient's natural size and configuration and being naturally secured between said mitral leaflets and heterologous portions of papillary muscle, wherein said sewing rim, said leaflets and said subvalvar apparatus are obtained entirely in one piece from a mammal; and at least two patches of heterologous material affixed to said heterologous portions of papillary muscle, wherein said at least two patches of heterologous material are configured to be sutured to the papillary muscle of the patient to satisfy said predetermined geometry of the chordal attachments.

2. The heart valve prosthesis of claim 1, wherein said mammals are selected from the group consisting of swine, ovine and bovine.

3. The heart valve prosthesis of claim 1 which is of an anatomic and functionally specific design that permits anchoring of the substitute to both the papillary muscles and to a mitral rim of the recipient.

4. The heart valve prosthesis of claim 1, wherein said heterologous portions of papillary muscle are secured to said pericardial patches by sutures selected from the group consisting of mono and polyfilament sutures.

5. The heart valve prosthesis of claim 1, wherein each said chordal attachment is fixed between said pericardial patches by sutures selected from the group consisting of mono and polyfilament sutures.

6. The mitral valve prosthesis of claim 1, wherein said two patches of heterologous material comprise synthetic material.

* * * * *